(12) United States Patent
Paulos

(10) Patent No.: US 8,512,377 B2
(45) Date of Patent: Aug. 20, 2013

(54) SUTURE ANCHORING ASSEMBLIES AND METHODS OF USE

(76) Inventor: Lonnie E. Paulos, Pensacola Beach, FL (US)

( * ) Notice: Subject to any disclaimer, the term of this patent is extended or adjusted under 35 U.S.C. 154(b) by 0 days.

(21) Appl. No.: 13/241,466

(22) Filed: Sep. 23, 2011

(65) Prior Publication Data

US 2012/0010657 A1  Jan. 12, 2012

Related U.S. Application Data

(62) Division of application No. 12/245,714, filed on Oct. 4, 2008, now Pat. No. 8,052,719.

(60) Provisional application No. 61/041,579, filed on Apr. 1, 2008.

(51) Int. Cl.
*A61B 17/04* (2006.01)

(52) U.S. Cl.
USPC ........................................... 606/232

(58) Field of Classification Search
USPC ................. 606/213, 215–217, 232, 198, 200, 606/300–301, 311; 623/13.13–13.14, 19.11, 623/23.72; 600/103
See application file for complete search history.

(56) References Cited

U.S. PATENT DOCUMENTS

| | | | |
|---|---|---|---|
| 5,002,550 A | 3/1991 | Li | |
| 5,041,129 A | 8/1991 | Hayhurst et al. | |
| 5,324,308 A | 6/1994 | Pierce | |
| 5,462,561 A | 10/1995 | Voda | |
| 6,306,156 B1 | 10/2001 | Clark | |
| 6,592,610 B2 | 7/2003 | Beyar | |
| 6,626,916 B1 | 9/2003 | Yeung et al. | |
| 6,719,934 B2 | 4/2004 | Stinson | |
| 6,932,834 B2 | 8/2005 | Lizardi et al. | |
| 7,857,830 B2 | 12/2010 | Stone et al. | |
| 7,909,851 B2 | 3/2011 | Stone et al. | |
| 2002/0169477 A1 | 11/2002 | Demopulos et al. | |
| 2004/0015186 A1 | 1/2004 | Bittar | |
| 2004/0260345 A1 | 12/2004 | Foerster | |
| 2005/0159762 A1 | 7/2005 | Nuutinen et al. | |
| 2005/0277983 A1 | 12/2005 | Saadat et al. | |
| 2006/0122647 A1* | 6/2006 | Callaghan et al. | 606/213 |
| 2006/0178680 A1 | 8/2006 | Nelson et al. | |
| 2006/0184202 A1 | 8/2006 | Frazier et al. | |

(Continued)

OTHER PUBLICATIONS

Kim Jun Gyu, International Search Report and Written Opinion for PCT Application PCT/US09/033615, Mailed Sep. 25, 2009, Korean Intellectual Property Office.

(Continued)

*Primary Examiner* — Melanie Tyson
*Assistant Examiner* — Son Dang
(74) *Attorney, Agent, or Firm* — John J. Brooks, III; John Brooks Law LLC

(57) ABSTRACT

A suture anchor assembly and methods of use will now are disclosed for the repair of human or animal tissue defects. The suture anchor assembly is capable of being inserted into a tissue or bone while also being able to create an expanded profile when subjected to a retrograde force. This expanded profile anchors the assembly into the tissue or bone by a changing of position of elements of the assembly relative to other assembly elements. Embodiments of the suture anchor assembly and methods are capable of precisely positioning assembly elements in the tissue or bone to effectively repair the defects.

20 Claims, 10 Drawing Sheets

(56) References Cited

U.S. PATENT DOCUMENTS

| | | |
|---|---|---|
| 2006/0200177 A1 | 9/2006 | Manzo |
| 2006/0206063 A1 | 9/2006 | Kagan et al. |
| 2006/0217762 A1 | 9/2006 | Maahs et al. |
| 2006/0235413 A1 | 10/2006 | Denham et al. |
| 2006/0271073 A1 | 11/2006 | Lam et al. |
| 2007/0032821 A1 | 2/2007 | Chin-Chen et al. |
| 2007/0260259 A1 | 11/2007 | Fanton et al. |
| 2008/0114399 A1 | 5/2008 | Bonutti |

OTHER PUBLICATIONS

International Bureau of the WIPO, International Preliminary Report on Patentability (IPRP) for related PCT App. No. PCT/US2009/033615, filed Feb. 10, 2009, IPRP Mailed Oct. 14, 2010, Switzerland.

* cited by examiner

SUTURE ANCHORING ASSEMBLIES AND METHODS OF USE

CROSS-REFERENCE TO RELATED APPLICATIONS

This application is a divisional application of U.S. patent application Ser. No. 12/245,714, filed Oct. 4, 2008 which claims benefit of U.S. Provisional Patent Application No. 61/041,579, filed Apr. 1, 2008, the entire contents of both applications are incorporated herein by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The present invention relates generally to a systems and methods for securing sutures and other materials during surgical procedures. More particularly, embodiments of the present invention relate to systems and methods for suture fixation and methods designed for the placement of surgical anchors for the attachment of tissues associated with orthopedic surgeries. Embodiments of the present invention also relate to systems and methods designed to reduce, or bring into close approximation, pieces of torn or damaged soft tissue to facilitate tissue repair and healing.

2. Description of Related Art

Open and arthroscopic meniscal repair has become a mainstay for the orthopedic surgeon. In the 1960s and 70s partial or total mastectomy was the norm. As arthroscopy and arthroscopic skills advanced arthroscopic combined with open or all arthroscopic meniscal repair became the standard of care. Multiple studies have demonstrated the ability of the meniscus to heal, particularly in the vascular zone which is in the first 3 mm of its capsular attachment. With advancement of arthroscopic meniscal repair tools more and varying types of meniscal tears have been successfully repaired.

The present weaknesses of meniscal repair systems are several. First the gold standard has been the "inside out" meniscal repair system. With this method, cannulae are passed through skin portals, and use long needles with sutures attached that are passed through the cannulae, through the knee joint, across the defect and out of the knee to be retrieved through an open incision and then tied against the deep capsular structures away from neurovascular structures. This technique allows for precise placement of sutures in the meniscus.

One of the problems associated with these types of procedures is the time and number of intubations needed to perform the various procedures endoscipically. In addition, this technique does not allow for precise placement of sutures thru the capsule, and therefore there is potential for neurovascular injury.

The outside-in techniques involve passing sutures through needles at the joint line across the tear, and then tying one end of the sutures together and tying the other ends of the sutures directly onto the capsule. Alternative techniques allow the sutures to be passed across the defect and tying the suture back on itself on the capsule. One advantage to this technique is that there is a low risk of neurovascular injury, since needles are passed thru precise thru the capsule. Potential disadvantages of the outside-in technique is that suture placement thru the meniscus may not be precise as well as difficulty in reducing the defect and opposing the edges while passing the sutures.

In the past 15 years "all inside" devices have been developed for meniscal repair. These devices were developed in order to obviate the need for posterior corner incisions medial or lateral and to reduce the risk of neurovascular damage as a result of the surgery. These devices are deployed through the arthroscopic portals and either oppose the meniscal fragments and/or push a pre-tied knot onto the body of the meniscus. The present devices have created articular lesions due to protrusion as well as partially deployed devices that are proud.

Systems and methods such as that disclosed in U.S. Pat. Pub. No. 2006/0178680 Nelson et. al. illustrate some embodiments of an all-inside solution.

The all inside systems are limited by how accurate they are when repairing a meniscus and thus have never enjoyed as good a success rates as the inside out devices referenced above. Because the all inside devices are so large it is virtually impossible to accurately pass a suture and/or meniscal device into the under surface of the meniscus, thus the majority of the devices are passed on the top surface in an attempt to pinch the lower inferior portions together. This technique in actuality leaves the tear distracted on its inferior surface. Although many devices have been fabricated for all-inside meniscal repairs, which can be done endoscopically without the open-skin incision, the incidence of re-tear among patients who have undergone the procedure is higher over time compared with that for patients who were given inside-out permanent sutures There is a benefit therefore from providing a suture anchor assembly and methods of use that allow accurate placement of the suture and suture anchor. There is also a benefit from providing assemblies and methods that minimize the number of incisions required for use.

Bone Anchor Systems:

There are numerous bone anchors with sutures attached that allow tissues to be approximated to specific bone attachment sites. Most systems deploy a three-step system wherein the hole is drilled, anchor placed and then the anchor holder removed and the anchor set by pulling on sutures. If the bone is of questionable quality, the anchor may only temporarily hold and loosen later through the rehabilitation phases. Also, if the first step of drilling a hole can be eliminated then it would be expected that the anchor would hold more securely, particularly in porous bone.

Systems such as those disclosed in U.S. Pat. Pub. No. 2007/0032821, Chao et. al. and U.S. Pat. Pub. No. 2006/0217762 Maahs et. al. show anchor systems that expand into an opening, however, they are not structured to open into and secure an element in bone.

Other systems rely on an anchor to flip, based on a second suture being placed at the end opposite the attached suture. There are also systems that anchor by means of screwing in or anchoring by means of flexible hooks.

There is a therefore a benefit from providing a suture anchor assembly and method of use that can be easily inserted and deployed through expansion.

BRIEF SUMMARY OF THE INVENTION

The suture anchor assembly is an assembly that is capable of being inserted into a tissue or bone in a forward direction while also being able to create an expanded profile when subjected to a retrograde, or opposite direction, force. This expanded profile generally anchors and secures the assembly into the tissue or bone by a changing of position of elements of the assembly relative to other assembly elements. This changing of position creates an expanded profile of the assembly in the tissue which helps to frictionally engage the tissue and anchor the assembly. Embodiments of the assembly and methods of the present invention provide for the accurately positioning and of anchoring of elements to fix sutures in tissue or bone.

In an embodiment, the suture anchor assembly for anchoring a suture in a tissue comprises a first body portion, a second body portion having a force connector and a means to connect the first body portion and the second body portion whereby a retrograde force on the force connector causes the first body portion to engage a tissue and secure the suture anchor assembly in the tissue.

In an embodiment, the suture anchor assembly includes the first and second body portions being planar shaped and the suture anchor assembly further includes a cannula having a slot shaped hollow portion to receive the planar body portions whereby the position of the first and second body portions can be controlled by the position of the slot shaped hollow portion.

In an embodiment, the suture anchor assembly further comprises a needle, a means of connecting the needle to the first body portion and a retrograde force element capable of connecting to the second body portion force connector.

In an embodiment, the suture anchor assembly further includes the first body portion being elongated, the means to connect the first body portion and the second body portion comprises a connector connecting a first connection point on the first body portion and a second connection point on the second body portion and the location of the force connector relative to the first body portion and the first connection point causes the first body portion to pivot relative to the second body portion when a retrograde force is applied to the force connector.

In an embodiment, the suture anchor assembly further includes the first body portion being capable of compressing to form a front end and a expansion end and the expansion end of the first body portion being biased to expand whereby a retrograde force on the force connector cause the expansion end to expand and engage the tissue and secure the suture anchor assembly in the tissue.

In an embodiment, the suture anchor assembly includes the first body portion being capable of being compressed to form a front end and a expansion end, the means to connect the first body portion comprising a collar on the first body portion to receive the second body portion and the expansion end of the first body portion being biased to expand whereby a retrograde force on the force connector forces the second body portion to expand the first body portion whereby the expansion end engages the tissue and secures the suture anchor assembly in the tissue.

In an embodiment, the suture anchor assembly comprises an impactor, an expandable first body portion having a distal collar and a proximal collar and a second body portion having a force connector whereby a retrograde force on the force connector forces the second body portion against the distal collar and a forward force on the impactor transfers the forward force to the proximal collar whereby the first body portion expands to secure the suture anchor assembly in the tissue.

In an embodiment, the suture anchor assembly further includes a delivery rod and a means to connect the delivery rod to the force connector whereby a force applied to the delivery rod is transferred to the second body portion.

In an embodiment, the suture anchor assembly further includes a means to retain the expansion of the first body portion to secure the suture anchor assembly in the tissue.

In an embodiment, a method of tissue repair comprises providing a suture anchor assembly having a retrograde suture, inserting the suture anchor assembly into a tissue, applying a retrograde force on the retrograde force element to cause the suture anchor assembly to engage the tissue and secure the suture anchor assembly in the tissue and anchoring the retrograde force element to secure the suture anchor assembly.

In an embodiment, the step of inserting a suture anchor assembly further includes inserting a needle connected to the suture anchor assembly and passing the needle and suture anchor assembly through the tissue.

In an embodiment, the suture anchor assembly further includes a first body portion connected to a second body portion connected to the retrograde suture and the step of applying a retrograde force on the retrograde force element further includes causing the first body portion to engage the tissue.

In an embodiment, the suture anchor assembly is planar and further comprises a cannula having a slot shaped hollow portion to receive the planar suture anchor assembly and the step of inserting the suture anchor assembly further includes positioning the insertion of the planar anchor assembly by the position of the slot shaped hollow portion.

In an embodiment, the method of tissue repair further includes repeating the step of inserting the suture anchor assembly and applying the retrograde force with at least one second suture anchor assembly having a second retrograde suture and the step of anchoring the retrograde force element further comprises anchoring the retrograde force element to the second retrograde force element to secure the suture anchor assemblies.

In an embodiment, the step of inserting a needle includes inserting the needle through a cannula.

In an embodiment, the first body portion is elongated and the step of applying a retrograde force to the retrograde force element causes the elongated first body portion to pivot relative to the second body portion and engage the tissue.

In an embodiment, the first body portion is capable of being compressed to form a front end and a expansion end, the expansion end of the first body portion expands when not compressed and the step of applying a retrograde force on the retrograde force element includes causing the expansion end to expand and engage the tissue.

In an embodiment, the first body portion is capable of being compressed to form a front end and a expansion end, the first body portion is connected to the second body portion by a collar on the to receive the second body portion, the expansion end of the first body portion expands when not compressed and the step of applying a retrograde force on the retrograde force element includes forcing the second body portion to expand the first body portion where the expansion end expands and engages the tissue.

In an embodiment, a method of anchoring a suture into a tissue comprises providing a suture anchor assembly with an expandable first body portion, a second body portion and a force connector connected to the second body portion; inserting the expandable first body portion and second body portion of a suture anchor assembly into a tissue; expanding the first body portion of the suture anchor assembly by applying a retrograde force to the force connector to secure the suture anchor assembly in the tissue; and attaching a suture to the suture anchor assembly.

In an embodiment, the step of inserting the second body portion further includes applying a first forward force on a sharpened distal end of the second body portion and the step of expanding the first body portion further includes applying the retrograde force to a distal end of the first body portion and applying a second forward force on a proximal end of the first body portion expanding the first body portion.

In an embodiment the step of expanding the first body portion further includes applying the retrograde force by forcing a wedge shaped proximal end of the second body portion into a collar of the distal end of the first body portion and applying the second forward force with a impactor whereby the retrograde force and the second forward force expands the outer dimension of the first body portion.

DETAILED DESCRIPTION OF THE INVENTION

A suture anchor assembly and methods of use will now be described in detail with reference to the accompanying drawings. Although embodiments are described for the repair of meniscal defects, it is understood that the methods and systems described can be use for the repair of other human or animal body defects. In particular it is contemplated that other embodiments of the invention can be use for repair and suture anchoring to bone or other tissues. Notwithstanding the specific example embodiments set forth below, all such variations and modifications that would be envisioned by one of ordinary skill in the art are intended to fall within the scope of this disclosure.

Throughout this description, a retrograde force means a force applied generally opposite of the direction of insertion of the assembly. Additionally, the verbs anchor and secure as used throughout this description mean to hold fast or otherwise fix or fasten.

Embodiments of the suture anchor assembly are shown in FIGS. 1-5C, 7A-7B and 9A-9B.

Figure 1:
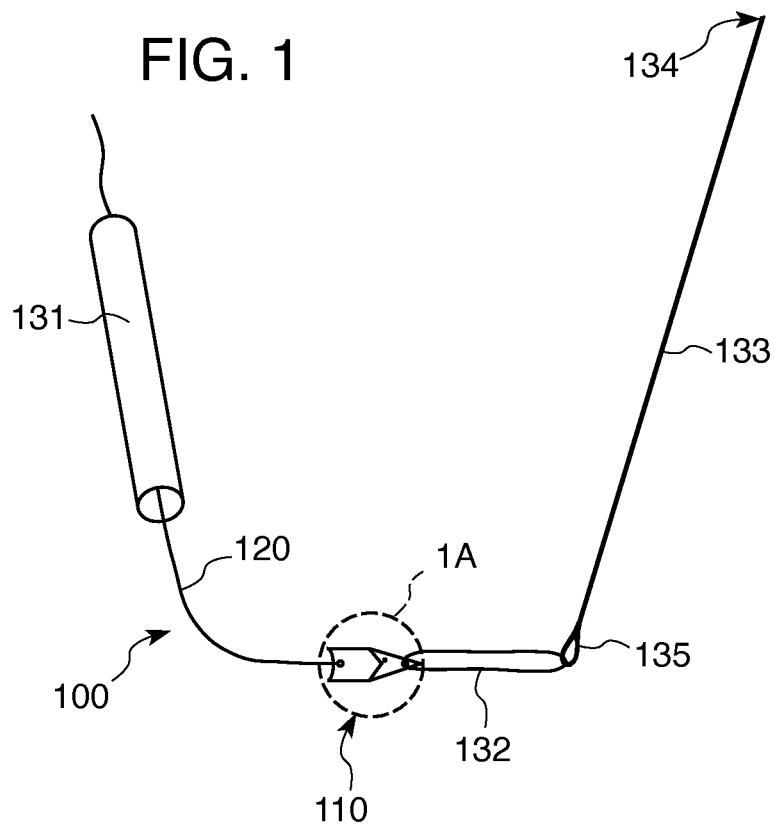
FIG. 1. A top view of one embodiment of the suture anchor assembly.

Meniscal Suture Anchor Assembly:

One embodiment of the suture anchor assembly is shown in FIG. 1. The suture anchor assembly 100 shown and described is a device that provides elements to allow new combinations of some features of the "inside-out" and "all-inside" solutions. This solution takes advantage of the accuracy and reliability of inside-out and outside-in suture solutions but can result in a device with all-inside features once the system has been deployed. Thus, by using this assembly outside incisions can be minimized while the accuracy and effectiveness of the inside-out system can be duplicated.

The assembly disclosed provides a solution that can be accurately placed around the defect, can be placed with fewer incisions and can be positioned to reduce the incidence of protrusions that may irritate the tissue or bone around the defect.

As shown in FIG. 1, one embodiment of the suture anchor assembly 100 comprises at least one set of a retrograde force element 120, a button 110 and a delivery system.

The retrograde force element 120 is connected to the button 110 by a force connector 113. The retrograde force element 120 is used to deploy and anchor the button 110. As shown in FIG. 1, the retrograde force element 120 may comprise a retrograde suture that provides the retrograde force and also secures that suture and anchor pair to another suture/anchor pair so that the defect is repaired or reinforced. Any type of surgical suture is suitable for use as a retrograde suture with this assembly. It is also understood that other types of retrograde force elements can be used to deploy the anchor and secure assembly elements and tissue together. These other types of retrograde force elements may include, but not be limited to other securing elements such as rods, pins, staples and other materials that can transfer and maintain a tensile force.

Figure 1A:
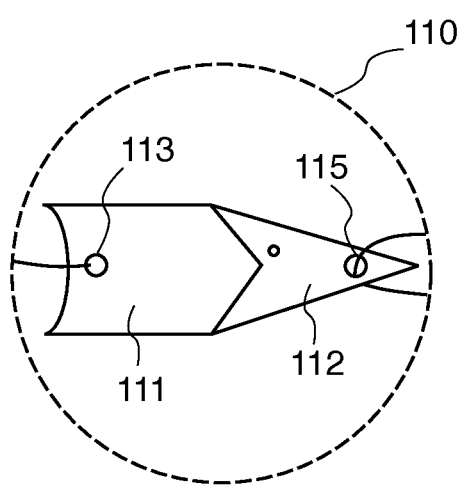
FIG. 1A. A top view of one embodiment of a button.

As detailed in FIG. 1A, the button 110 is a rigid or semi-rigid element with a force connector 113. The button 110 is shaped to change or transform shape when a retrograde force is applied to the force connector 113. Although not required, this transformation can be done with some degree of control of the profile of the button. This change of shape allows the button 110 to anchor in the tissue and counter that same, or a different retrograde force. The button 110 can be made of biocompatible materials that include, but are not limited to metals, metal alloys or non-metallic materials such as nylon, polyethylene, polypropylene or any combination thereof. The force connector 113 provides the connection through which forces are transferred to the button 110. Although shown in this embodiment as a suture tie for the retrograde suture, the force connector 113 can comprise any element capable of connecting the retrograde force element to the button in a way that a tensile force can be applied and maintained on the force element. Suitable connection elements include, but are not limited to mating threads, clips, hooks, holes, permanent adhesive connections or any combination thereof.

Figure 2A:
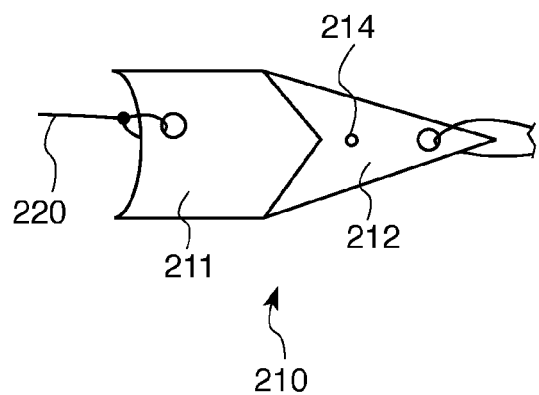
FIGS. 2A-2D. A top view of multiple embodiments of the button in an insertion and deployed position.
Figure 2B:
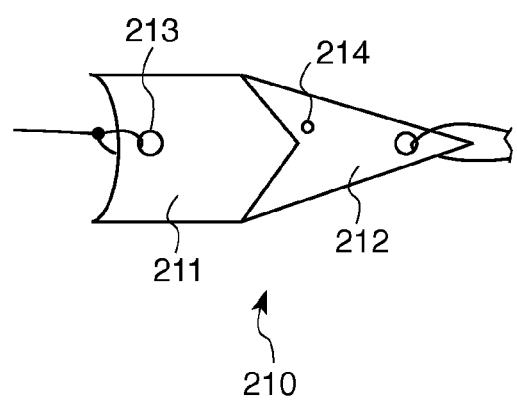
Figure 2C:
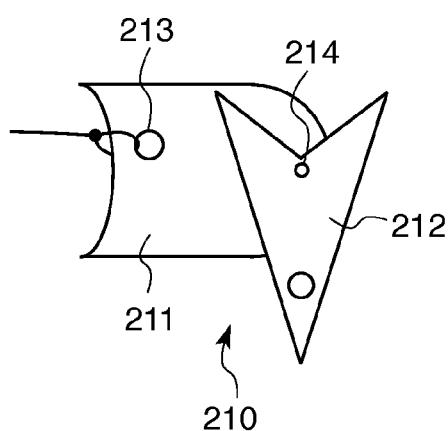
Figure 2D:
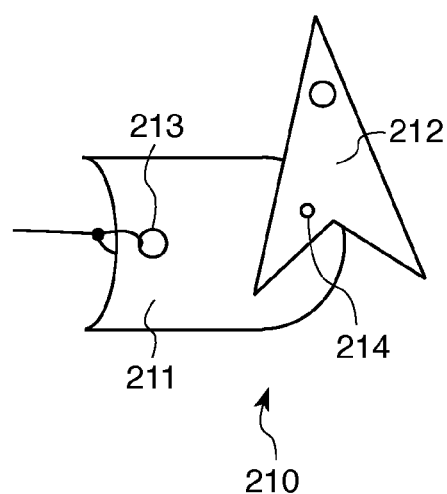

In the embodiment shown in FIGS. 2A-2D, the button 210 comprises an expandable first body portion 212 and second retrograde force body portion 211 and a means to connect the two portions. In this embodiment, the expandable body portion 212 is a generally elongated and pointed section and the retrograde force body portion 211 is generally a broad section. The expandable and retrograde force portions each have a connection point and are connected to each connection point by a connector 214. The connection points comprise a means of receiving a connector such as a hole, slot or adhesive and the connector comprises a means of connecting the two body portions such as, but not limited to a pivot hinge or rivet. The retrograde force element in this embodiment comprises a retrograde suture 220. The retrograde suture 220 is connected to the retrograde force portion 211 of the button through the force connector comprising a suture tie 213. This suture tie 213 can be any method of securing a suture to the body portion. The suture tie as shown in FIGS. 2A 2D comprises an off-center hole in the retrograde force portion 211.

The means to connect the body portions of the button can include any connecting methods that allow the two portions to pivot and/or rotate about the connection points. For example, it is contemplated that the connector 214 may be comprised of a protrusion, hook or other connection element on one body portion that is capable of being connected to a complementary hole, slot or other connecting element on the other body portion.

The interoperation of the suture tie 213, the connection points and the two button body portions are such that a retrograde force on the suture tie urges the expandable body portion 212 to rotate or otherwise move in a direction at an angle different than the retrograde force. This rotation or movement causes an expanded profile of the button which frictionally increases the resistance that can be provided by the button and expansion suture. The elongated shape, where the length of the portion in an insertion position is greater than its width, of the expandable body portion causes this expanded profile when the expandable portion is moved about the connector. This interoperation to cause the expandable body portion to rotate can be provided by a location of the suture tie relative to the connection points. One example of this interoperation is shown in FIG. 2A where the location of suture tie 213 is off the center of the retrograde force body portion 211 while the connector 214 and connection point is located in the center of both button portions. As shown in FIG. 2B, a retrograde force on the suture tie 213 cause a force on the connector 214 that causes the expandable body portion 212 to pivot and/or rotate at an angle different than the direction of the retrograde force. Alternately, as shown in FIGS. 2C-2D, the location of the connection points on the expandable body portion to be off-center while the suture tie is on the center line of the body portion.

It is also contemplated to have the shape of the body portions such that a retrograde force on the button causes the expandable body portion 212 to pivot and/or rotate. For example, the expandable body portion can have a barb or other protrusion on its expansion end that causes that portion to rotate when partially retracted by the application of a retrograde force.

In some embodiments, the shape of the button can be made such that it minimizes the possibility of undesired protrusions when the button is deployed. An undesired protrusion is a protrusion that can damage other tissues or bone. These undesired protrusions are different than the desired protrusions caused the normal expansion of the button. For example, as in FIGS. 2A-2D, the shape of the button can be made so that it is primarily a two-dimensional planar shape with a minimal profile in a third dimension. This allows the button to be inserted and to expand primarily in dimensions parallel to particular surfaces, such as the articular cartilage surfaces of the knee, while minimizing the potential for expanding perpendicular to those surfaces. This minimizes the possibility of having protrusions that may damages these surfaces or tissues. It is also contemplated that the shape of the cannula can be made to assist in the positioning of the button in deployment. This can be provided by, but not limited to an inner bore shape of the cannula that is primarily slot shaped to cooperate with a primarily two-dimensional shaped button. This would allow the profile of the button in the tissue to be controlled by the rotational position of the cannula. Other cooperating shapes of button and cannula bores are contemplated such as ovals, circles and rectangles.

Referring back to the embodiment shown in FIG. 1, the suture anchor assembly also comprises a delivery system for the button 110 and retrograde force element 120. As shown in the embodiment in FIG. 1, this delivery system comprises a needle 133, a traction suture 132 and a cannula 131.

The needle 133 is used to position and insert the button 110 and retrograde force element 120. The needle 133 comprises an elongated rod with a sharpened distal end 134 and a proximal end 135 that has an eye or other means to allow connection to the traction suture 132. As an example, and not for limitation, 12 inch long needles made of stainless steel or Nitinol are suitable for use with this assembly.

The traction suture 132 is connected to the needle's proximal end 135 and the button 110. Preferably, the traction suture is connected to a traction suture tie 115 on the sharpened end of button's expandable body portion 112. The traction suture 132 is used to connect the needle 133 and the button 110 allowing the button to be pulled through the tissue and the defect to be deployed on one side of the defect. Any type of surgical suture or similar connection means is suitable for use as a traction suture with this assembly.

The retrograde force element 120 is connected to the force connector 113 on a retrograde force body portion 111 of the button 110.

The cannula 131 is used to help position and deploy the needle 133. The cannula 131 is a hollow element with a longitudinal extending bore to receive the needle, the traction suture, the button and the expansion suture. As an example, and not for limitation, 6 inch hollow cannula of about ⅜ inch in diameter is suitable for use with this assembly. In one embodiment, the distal end of the cannula is bent at angles to help guide the needles into the proper direction and position.

And although the delivery system embodiment described includes a traction suture connected to a traction suture tie and the eye of a needle, other means to connect the needle and the button are contemplated that include flexible, semi-flexible or substantially rigid connecting elements. Examples of these connecting elements include but are not limited to a directly mating connection between the needle and the button such as a threaded connection, one element hooking into an eye of another or one element clipping into a recess of another. Other examples of connecting elements include, but are not limited to a connector connecting the needle and the button such as a flexible hook, chain, wire, rods or other means to removeably connect the two elements.

Alternative Button Embodiments:

Alternative embodiments of the button are shown in FIGS. 3A-5B.

Figure 3A:
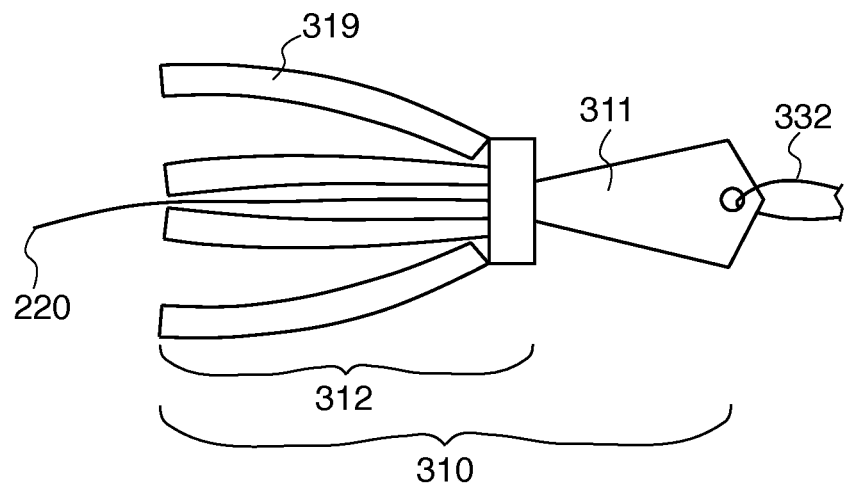
FIGS. 3A-3B. A top view of one embodiment of the button in an insertion and a deployed position.
Figure 3B:
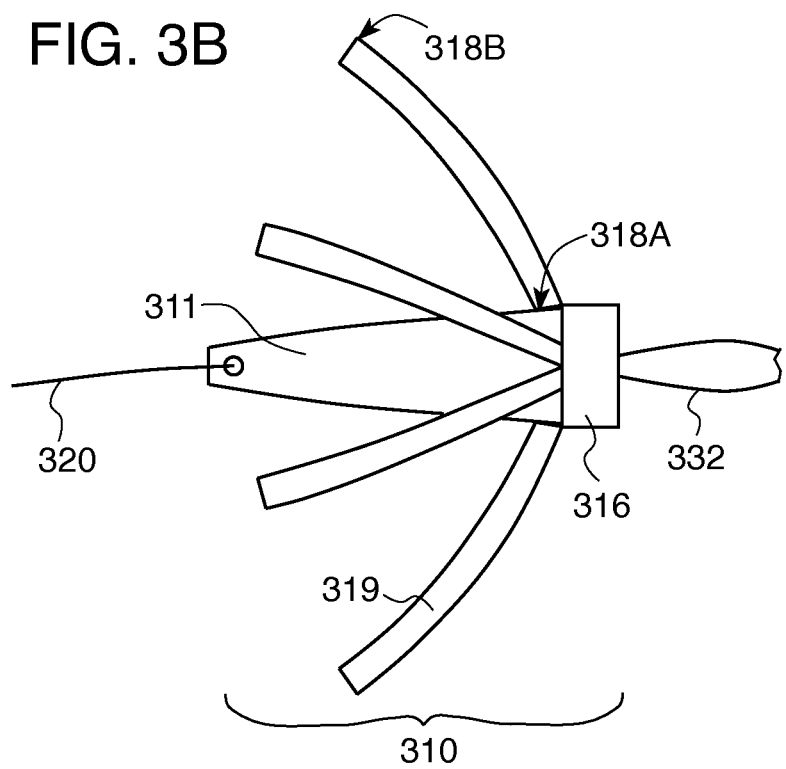

FIGS. 3A and 3B illustrate one embodiment of the button 310. In the illustrated embodiment, the button 310 comprises an expandable first body portion 312 comprising expansion fingers 319, a collar 316 and a retrograde force body portion 311 that is shaped as a rod. The retrograde force body portion 311 is connected to both the traction suture 332 and the retrograde suture 320 (retrograde force element) and is received into a collar 316. As shown in FIG. 3A, this embodiment is able to be inserted into a patient's body starting with the traction suture end. In the insertion position of FIG. 3A, the fingers are compressed to minimize the profile of the assembly during insertion. When sufficient tension is placed on the retrograde force body portion 311 from the retrograde suture side, the retrograde force body portion 311 retracts towards the expandable body portion 312 and into the collar 316, deploying the expansion fingers 319. The expansion fingers 319 engage the retrograde force body portion 311 so that the fingers are urged to expand when the rod retracts. As shown in FIG. 3B, the fingers have an angled end 318A on the end that connects with a collar 316. When the retrograde force body portion 311 is retracted, this angled end 318A is rotated about a connection to the collar 316 forcing the expansion ends 318B of the fingers 319 to expand. Other methods of cooperation between the fingers and the retrograde force rod so that the fingers expand are contemplated to include any types of angles for the angled end 318A and any type of tethered connection to the collar that allows the fingers 319 to move and expand.

As shown in FIG. 3B, the deployment of the fingers 319 enables the button 310 to act as an obstruction and anchor for the retrograde suture 320 connected to the button.

Figure 4A:
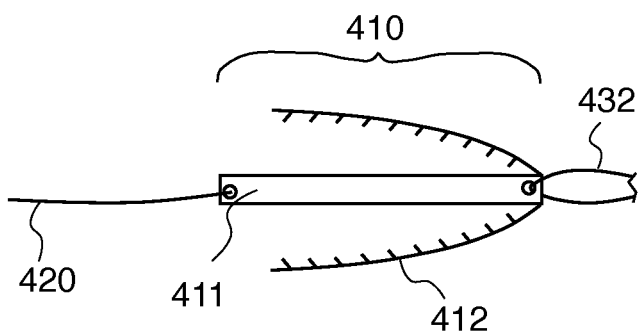
FIGS. 4A-4B. A top view of one embodiment of the button in an insertion and a deployed position.
Figure 4B:
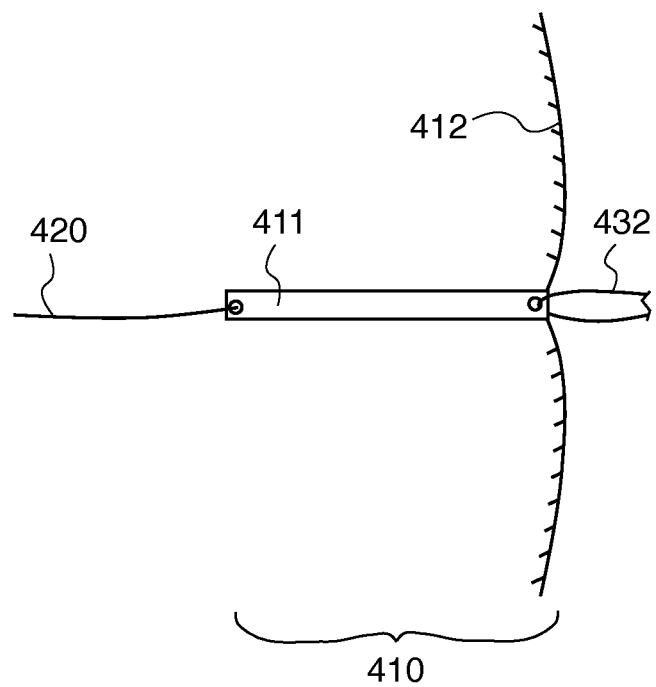

FIGS. 4A and 4B illustrate another embodiment of a button 410. In the illustrated embodiment, the button comprises an expandable first body portion 412 comprising a flexible hoop that is biased to expand and a second retrograde force portion 411 shaped like a bar. The retrograde force body portion 411 is connected to the traction suture 432 and the retrograde suture 420. As shown in FIG. 4A, this embodiment is able to be inserted into a patient's body starting with the traction suture end and the flexible hoop is folded back, or otherwise compressed against its bias to expand and to minimize its profile during insertion. When compressed, the end of the flexible hoop nearest the traction suture is the front end and the opposite end of the hoop is the expansion end. When placed in position, the expandable body portion 412 is expanded about its front end by a trip or by the release of tension on the hoop. As shown in FIG. 4B, the expansion and deployment of the expansion end of the expandable body portion 412 enables the button 410 to engage the tissue and act as an obstruction and anchor for the retrograde suture connected to the button 410.

The embodiments of anchoring sutures described above are also suitable for anchoring sutures to other body parts such as bones. One embodiment particularly suitable as a bone suture anchoring system is shown in FIGS. 5A and 5B and described below.

Figure 5A:
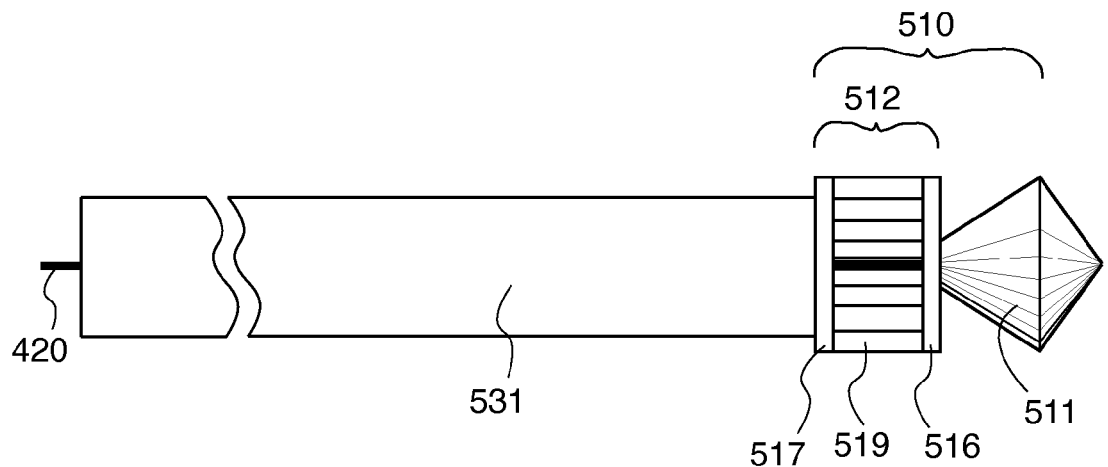
FIG. 5A-5B. A side view of one embodiment of the button in an insertion and a deployed position.
Figure 5B:
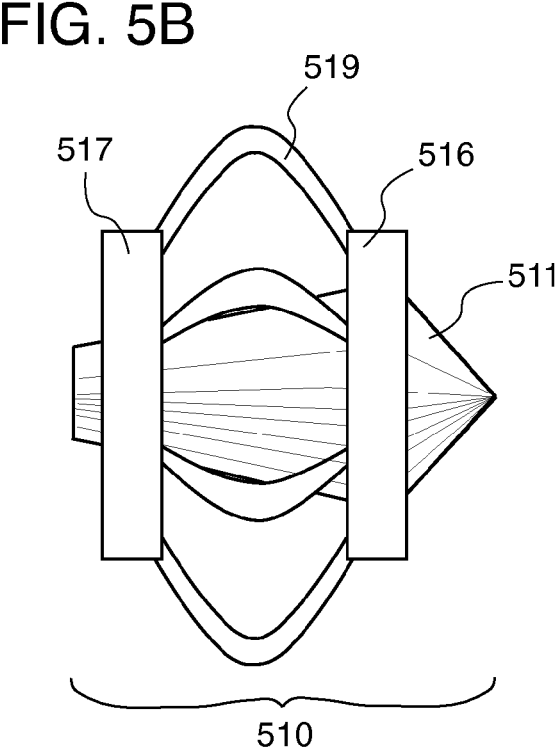

Bone Suture Anchor Assembly:

Referring to FIGS. 5A and 5B, another embodiment of the suture anchor assembly comprises an expandable first body portion 512 comprising one or more collars with expansion fingers 519, a second retrograde force portion 511 shaped as a trochar, a delivery rod 520 and an impactor 531. Although not limited to, this embodiment is particularly helpful for anchoring sutures to bone.

In this embodiment, the retrograde force body portion 511 is shaped as a wedge pin or trochar with sharpened distal end and a connectable proximal end including a force connector. In this embodiment, the force connector comprises a threaded portion to removably connect with the threaded end of the delivery rod 520. This retrograde force body portion 511 is preferably made from a rigid material such as a metal, plastic or a composite that allows a force to be applied to the threaded end while the sharpened end penetrates bone.

The delivery rod 520 is a rigid or semi-rigid element capable of receiving a force from one end of the rod and transferring that force to retrograde force body portion 511 of the button 510. The rod 520 is cable of receiving and transferring both a forward and retrograde force to the retrograde force body portion 511. The distal end of the rod is configured to mate with the force connector of the retrograde force portion of the button. In this embodiment, the delivery rod distal end is threaded to mate with the force connector. It is contemplated that either of these elements may have the male or female elements of a threaded connection.

Although this embodiment has a delivery rod 520 that connects with retrograde force portion 511 of the button 510 with the use of threaded connections, it is also understood that other means of connecting the delivery rod 520 and the button 510 are possible such as but not limited to mating clips, buttons, protrusions or other connection means.

In this embodiment shown in FIG. 5A, the expandable body portion 512 comprises a proximal collar 517, a distal collar 516 each attached to one or more expanding fingers 519. The collars and fingers are configured so that when forces are applied to urge both collars together, the fingers 519 are forced to flexibly expand outward from the center of the body portion. FIG. 5B illustrates this embodiment in an expanded configuration. This expansion creates the larger profile of the button 510. Although the fingers 519 are able to flexibly expand, they are rigid enough to provide a frictional connection when expanded against bone or other tissue. The expandable body portion 512 of this embodiment can be made of materials that include, but are not limited to metals, metal alloys or non-metallic materials such as nylon, polyethylene, polypropylene or any combination thereof.

Figure 5C:
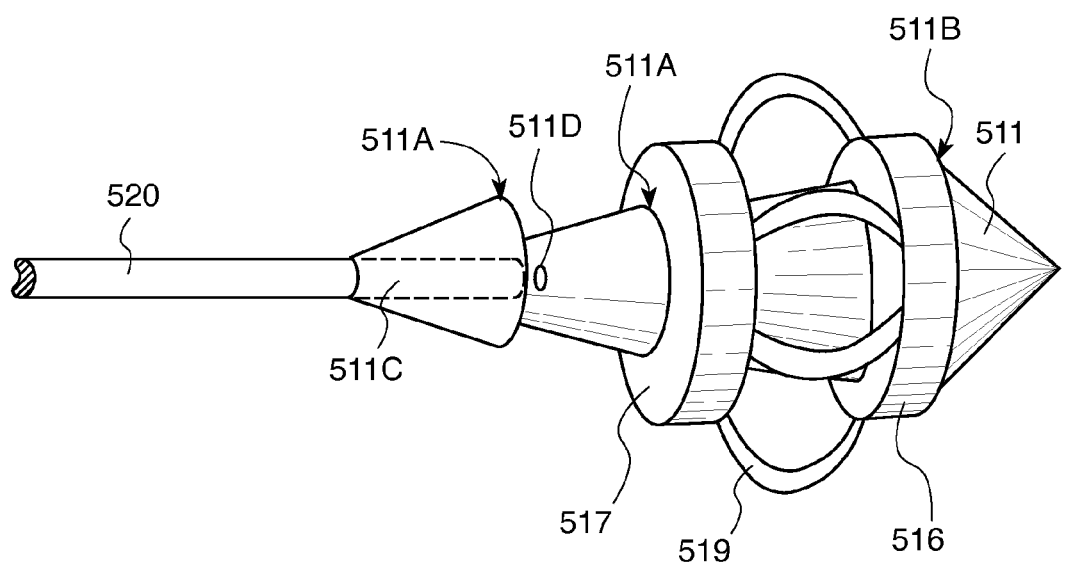
FIG. 5C. A side perspective view of one embodiment of the suture anchor assembly with the button in a deployed position.

In one embodiment, it is also contemplated that the shape of the retrograde force portion includes a hook, protrusion or other means to engage the proximal collar 517 so that the two collars can be retained together and the fingers 519 can be kept in their expanded position after deployment. For one embodiment shown in FIG. 5C, the engagement means comprises one or more protrusions 511A on the retrograde force body portion 511 that compress when forced through one direction of the bore of the proximal collar 517 and expand to prevent the collar from moving in the other direction to retain the collar in one position relative to the protrusions 511A. In this embodiment, the wedge shape of the distal end of the retrograde force body portion 511 creates a wedge edge 511B that transfers the retrograde force against the distal collar 516. The cooperation of the protrusions 511A engagement on the proximal collar 517 and the wedge edge 511B against the distal collar 516 retains the button 510 in a position where the fingers 519 are maintained in an expanded state after deployment. As shown in FIG. 5C, if there are multiple protrusions 511A, the retrograde force body portion 511 will urge the collars together until the fingers expand fully into the defect or bore and the protrusions will be retracted through the proximal collar to engage the proximal collar 517 in a tight position. As also shown in FIG. 5C, a threaded recess 511C provides one means to connect the delivery rod 520 with the retrograde force body portion 511. Also shown is FIG. 5C is an additional suture tie 511D to receive and secure a suture to the anchor assembly.

The impactor 531 is a rigid or semi-rigid element capable of receiving a force from one end of the impactor and transferring that force to the expandable body portion 512. In the embodiment shown, the impactor 531 is a rigid cannula with a longitudinal hollow bore to receive the delivery rod 520. In this embodiment, the bore is shaped to allow the delivery rod 520 to move within the bore while it is also shaped to provide a resisting force on the proximal collar 517 of the button 510. The impactor 531 is shaped to allow the required force to be applied. It is understood that this may require surfaces to either allow the force to be applied frictionally or for the surfaces to be shaped to allow a striking force to be applied. For example, and not for limitation, the impactor 531 may be shaped to have texture about its outer surface to allow the user to frictionally apply the forward force or it can include a flattened surface that would allow the impactor 531 to be struck by a device such as a hammer.

In this embodiment, the cooperation of the elements allows the anchor to be deployed without the need for a traction suture and needle.

It is understood and contemplated that the anchor elements, including the button elements, retrograde force elements and sutures, can be made with both resorbable and non-resorbable materials and each one has its individual characteristics which allow it to work best in tissue or in bone such as cortical and cancellous bone.

Figure 6:
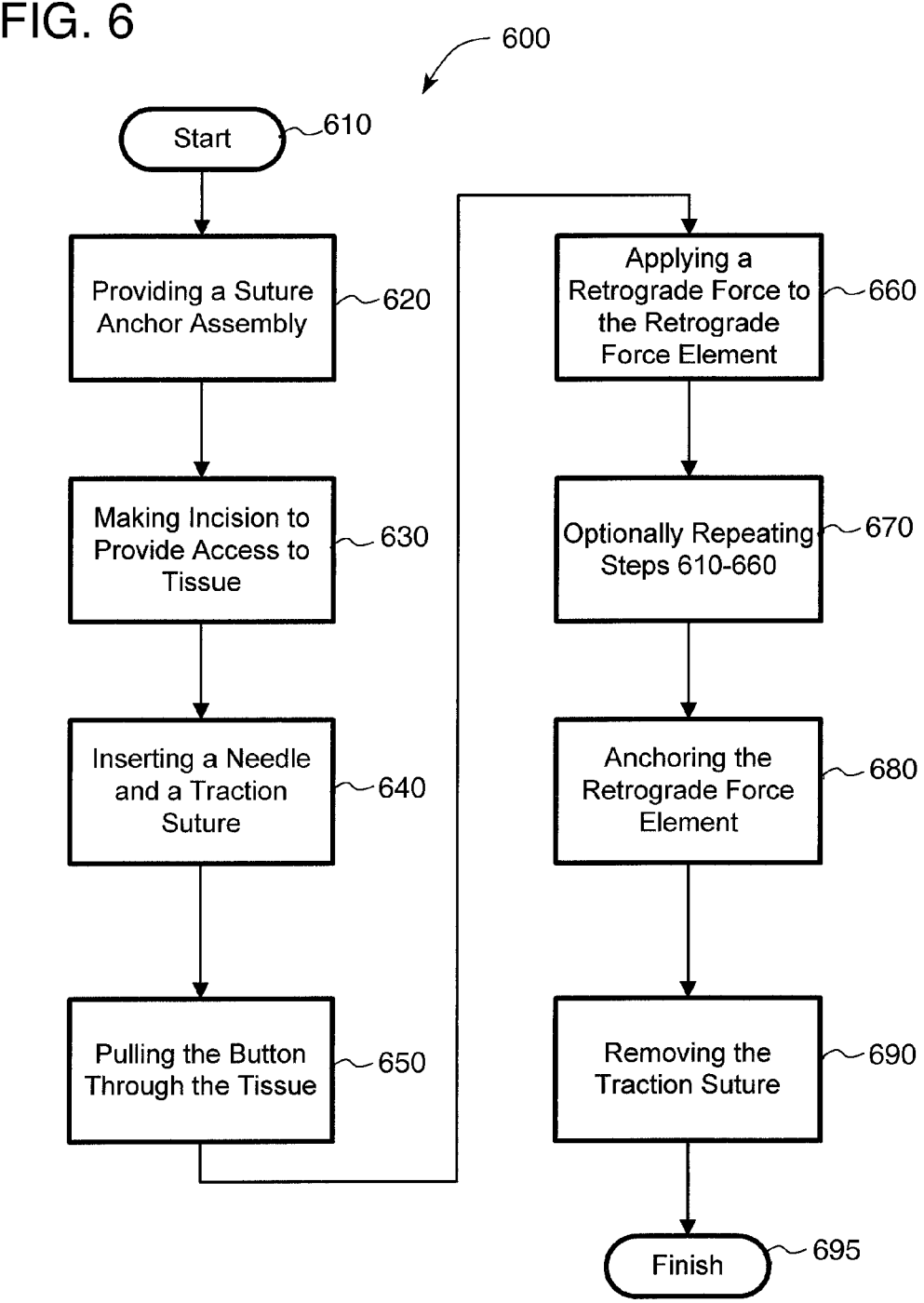
FIG. 6. A process diagram outlining one embodiment of the method of operating on embodiment of the suture anchor assembly.

Meniscal Repair Method with Meniscal Suture Anchor Assembly:

One method of operating one embodiment of the suture anchor assembly shown in FIG. 1 is shown as process steps in FIG. 6. Although particular embodiments of the suture anchor assembly are described, and particular uses of the methods are described, these uses and embodiments are used for illustration purposes and not for limitation. This method 600 comprises the steps of:

Following the starting step 610, a suture anchor assembly is provided as step 620. In one embodiment, the suture anchor assembly comprises a needle, a traction suture, a button, a retrograde force connector and a cannula. The needle is connected to the button with the traction suture and the retrograde force connector is also connected to the button.

Step 630 includes making a small incision to provide access to the tissue to be repaired. For meniscal repair embodiments, this includes making a small incisions on either the medial or lateral joint line down to the outer lining of the joint capsule.

Step 640 includes inserting the needle and traction suture of the suture anchor assembly through the cannula and joint lining and through the defect in the meniscus. The needle is passed from the inside of the joint to the outside while carefully protecting the neurovascular structures.

Figure 7A:
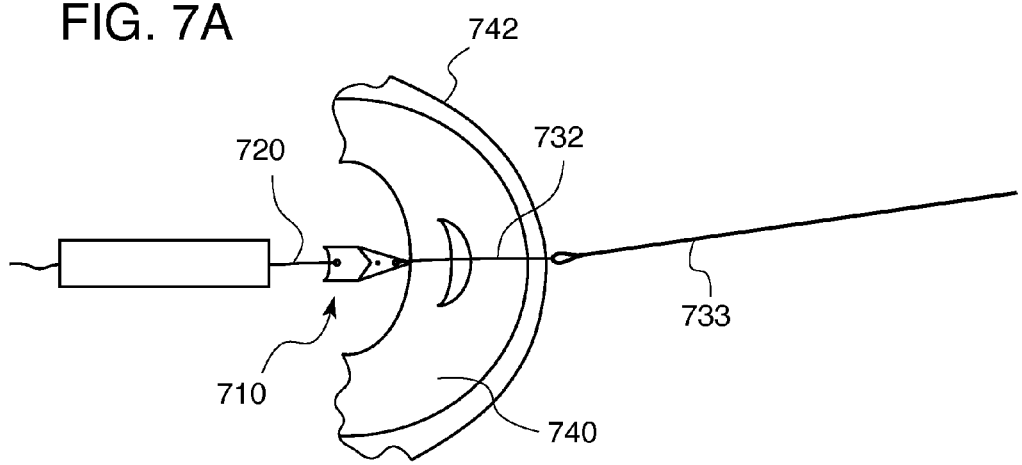
FIG. 7A-7B. A top view of one embodiment of the suture anchor assembly being inserted and deployed in a meniscal repair.

FIG. 7A illustrates the use of one suture anchor assembly in step 640 where the needle 733 is passed through a tissue 740, such as a meniscus, through the defect 741 and outside of the joint lining surface 742. FIG. 7A shows the other elements of the suture anchor assembly prior to pulling the button 710 and retrograde suture 720 (retrograde force element) into the meniscus 740 with the traction suture 732.

Step 650 includes pulling the button through the tissue with the needle and the traction suture. The button need not be pulled entirely through the tissue but may be pulled across the defect and into a position such that the button will anchor into the tissue on the opposing side of the defect. The buttons are preferably not placed near significant neuro-vascular structures. The buttons are also placed to make sure it is buried in the tissue so that no sharp edges are exposed to other tissues or bone.

In one embodiment for meniscal repair, it is beneficial, but not necessary, in this method to have the button shaped generally flat or planar so that its profile once inserted can be generally parallel to the surfaces of the knee joints to minimize the possibility of protrusions that would irritate the tissues of the joint. For control purposes, the hollow of the cannula can be shaped to receive the button and control its profile during insertion. For example, the button can be planar shaped and the hollow of the cannula can be slot shaped allowing a rotation of the cannula to rotation the planar position of the button.

In one embodiment, of meniscal repair, the final position of the buttons may also be pulled totally through the meniscus to include but not limited to, positions that rest on the outer surface of the meniscus or positions outside of the joint capsule.

Step 660 includes applying a retrograde force on the retrograde force element to deploy the button and urge the tissue defect into the desired position. Typically, but not necessarily, this desired position is to urge opposing edges of a defect together. The retrograde force on the retrograde suture is transferred to a retrograde force to the button which forces the button to deploy and anchor the expansion suture.

It is not necessary to perform step 660 prior to adding a second button and retrograde force element.

Although not required, step 670 includes repeating the above steps (610-660) for at least a second time. For embodiments where the retrograde force element is a retrograde suture, the placement of the needle and the retrograde suture into the tissue is such that it can form sutures such as, but not limited to vertical or horizontal mattress sutures to repair the meniscal defect.

Step 680 includes anchoring the retrograde force element to maintain the tissue defect in the desired position. For embodiments where the retrograde force element is a retrograde suture, the fixation arms of the sutures can be anchored by tying knots in or otherwise knotting the sutures separately or knotting the expansion sutures together to repair the defect.

Step 690 includes removing the traction suture. The traction suture and needle may be removed from the button at any time after the button is positioned properly. One method of removal is to have the traction suture configured as a loop through both the button and the needle whereby cutting one segment of the loop allows the entire suture to be pulled out of the button.

The method is finished with step 695.

Figure 7B:
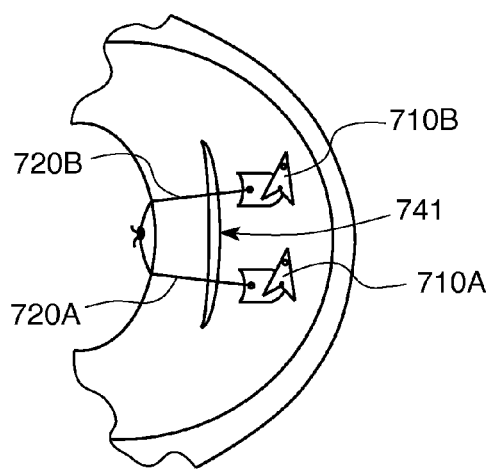

The result of this embodiment for a miniscal repair, as illustrated in 7B, are retrograde sutures 720 that are anchored on either side of a miniscal defect 741 to maintain the tissue 740 in a position to repair or promote healing of the defect. FIG. 7B shows two sutures 720A and 720B anchored by two buttons 710A and 710B across the tissue defect 741.

With this embodiment of the method, incisions that are normally needed in the inside-out procedures to secure the fixation arms of the sutures are not needed. Additionally, the ability to use needles to position the buttons and sutures allows more accurate position of the devices within the tissue and around neuro-vascular structures.

Other methods of use are contemplated as would be envisioned by those skilled in the art. For example, it is contemplated to have pre-tied knots in the sutures to either create a knot in a single suture or to tie two or more sutures together.

It is also contemplated that the method of using needles and traction sutures to position the anchor can be used with other suture anchor systems. Needles and elements to provide the function of the traction suture can be used with existing suture anchor systems.

It is also contemplated that the above method may be performed without the need to use a needle and traction suture to position the button. For these embodiments, it is envisioned that the button may be manufactured to include a distal end that can insert itself and the retrograde suture sufficiently or it can be designed to receive an element such as a guide pin that can be removed once the button is positioned properly. In these embodiments, it is also envisioned that the cannula or other guide means can be designed to provide the force to position the button for meniscal repair.

Although the above description is illustrative of the methods for use with meniscal repair, it is also contemplated that the methods can be applied to the repair of other tissues such as but not limited to stomachs and cartilage associated with joints such as a hip, elbow or shoulder.

Figure 8:
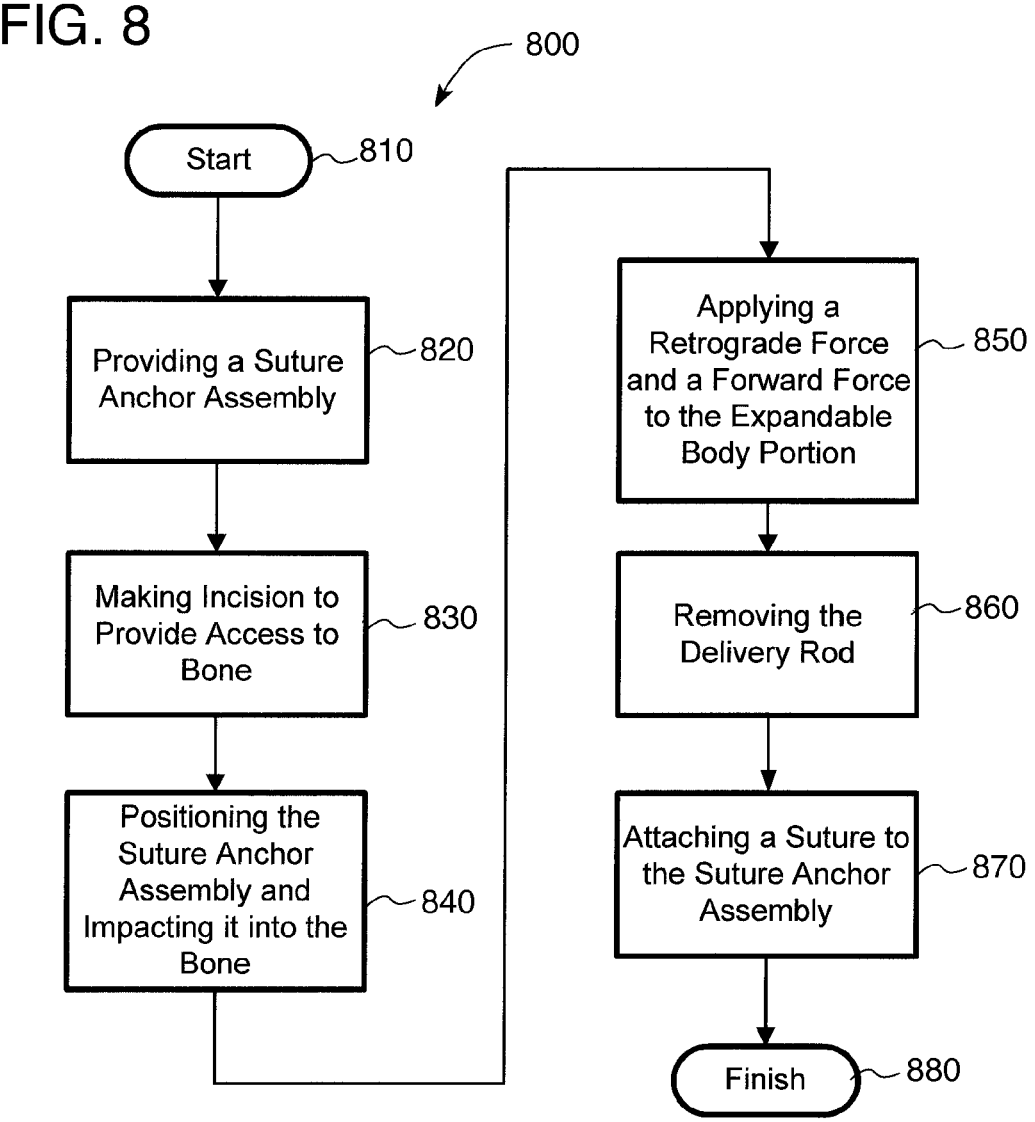
FIG. 8. A process diagram outlining one embodiment of the method of operating on embodiment of the suture anchor assembly.

Bone Anchoring Method with Bone Suture Anchor Assembly:

One method 800 of using one embodiment of the bone suture anchor assembly shown in FIG. 5 is outlined in FIG. 8 and described below.

Figure 9A:
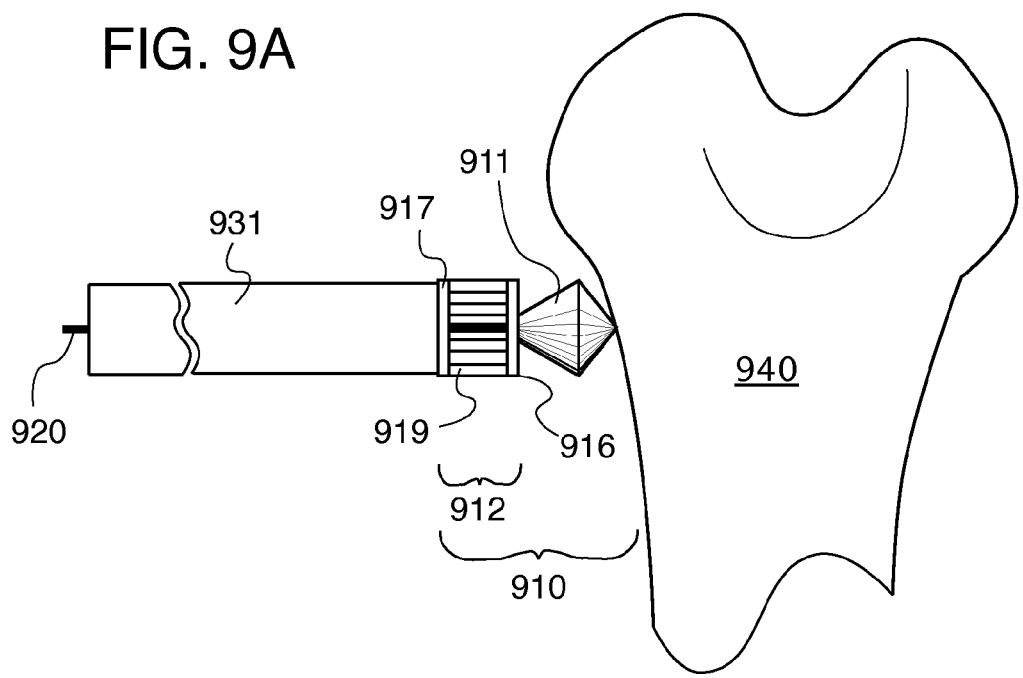
FIG. 9A-9B. A top perspective view of one embodiment of the suture anchor assembly being inserted and deployed to secure a suture in bone.

Following step 810, a bone suture anchor assembly is provided in step 820. In one embodiment, the assembly includes an expandable first body portion comprising one or more collars with expanding fingers, a second retrograde force portion shaped as a trochar, a delivery rod and an impactor. As shown in FIG. 9A, the delivery rod 920 is connected to the proximal end of the retrograde force portion 9110. The delivery rod 920 is received through the proximal collar 917 and distal collar 916 of the expandable first body portion 912 and the impactor 931 is placed around the delivery rod 920 forcing the expandable body potion 912 to be positioned between trochar 9110 and the impactor 931.

Step 830 includes making an incision to provide access to the bone.

Step 840 includes positioning the sharpened end of the trochar against the bone and impacting the anchor assembly into the bone. This step typically includes striking the delivery rod with a weighted object such as a hammer. This forward force is transferred through the delivery rod to the sharp end of the trochar causing the trochar to penetrate the bone. In this step, the sharp trochar is inserted into the bone followed by the insertion of the expandable body portion. The size and shape of the trocar is such that its penetration of the bone forms a cavity of a size to allow the first body portion to also penetrate the bone. Embodiments of this assembly can be inserted into the bone with or without pre-drilling.

Once the trochar and expandable first body portion have penetrated the bone, step 850 includes applying a retrograde force the retrograde force element. In one embodiment, this retrograde force is applied by the delivery rod that is connected to the trochar by the cooperation of the threaded end of the delivery rod and the threaded end of the trochar. The application of this retrograde force subjects the trochar and the distal end of the expandable body portion to that retrograde force while the proximal end of the expandable body portion is subjected to an opposite, forward force from the impactor. These opposing forces force the trochar to pass through the middle of the anchoring device until the outer dimension of the trochar can no longer fit the interior dimension of the distal collar of the first body portion. When the trochar can no longer pass, the retrograde force is transferred to the distal collar forcing the collar to move toward the proximal collar and expand the first body portion until the body portion can no longer expand. This anchor will expand until its profile generally fills the bore created by the trochar. At that point the expanding trochar will stop its retrograde progression. In this position, the anchor is frictionally engaged and held in the bone bore.

Although step 850 includes pulling the trochar retrograde into the expandable body portion, it is also contemplated that the anchor assembly can engage the tissue by maintaining the position of the trochar and forcing the expandable body portion onto the shape of the trochar. This forcing can be applied by the impactor and can also cause the expandable body portion to expand into the bore.

Figure 9B:
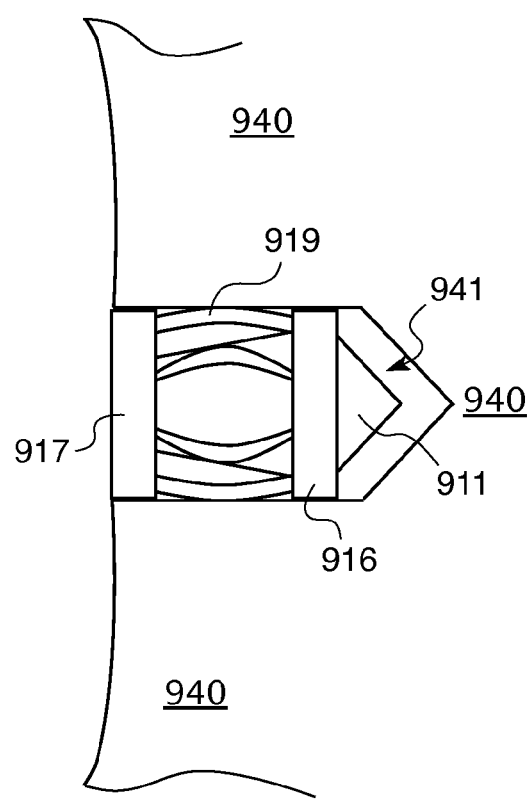

FIG. 9B illustrates this embodiment of the bone suture anchor assembly having been impacted into the bone.

Step 860 includes removing the delivery rod from the trochar.

Step 870 includes attaching a suture or other surgical device to the anchor assembly's first or second body portion. The suture is attached to the anchor assembly under tension which keeps the expandable body portion in an expanded position.

The method is finished with step 880.

The result of this embodiment is shown in FIG. 9B. The trochar 911 (retrograde body portion) is retracted against the distal collar 916. The proximal collar 917 has been retained to urge the fingers 919 to expand. Once expanded, the fingers 919 are frictionally engaged within an opening 941 in the bone originally caused by the trochar 911 being impacted into the bone.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A suture anchor assembly comprising:
   an expandable first body portion having a distal collar and a proximal collar;
   a second body portion having a sharpened distal end to penetrate bone; and
   the second body portion having a force connector whereby a retrograde force on the force connector forces the second body portion against the distal collar and a forward force on the proximal collar forces the first body portion to expand to secure the suture anchor assembly in a tissue.

2. The suture anchor assembly of claim 1 further comprising an impactor configured to transfer the forward force to the proximal collar.

3. The suture anchor assembly of claim 1 wherein the first body portion further comprises expansion fingers positioned between the distal and proximal collar whereby when the first body portion expands, the expansion fingers flexibly expand outward from the first body portion to secure the suture anchor assembly in the tissue.

4. The suture anchor assembly of claim 1 wherein the first body portion comprises a resorbable material.

5. The suture anchor assembly of claim 1 wherein the second body portion further comprises a suture tie whereby the suture tie is configured to retain a suture to the second body portion.

6. The suture anchor assembly of claim 1 further comprising:
   a delivery rod; and
   a means to connect the delivery rod to the force connector whereby a retrograde force applied to the delivery rod is transferred to the second body portion.

7. The suture anchor assembly of claim 6 wherein the force connector comprises a threaded recess in a connectable proximal end of the second body portion and the means to connect comprises a threaded distal end of the delivery rod configured to mate with the threaded recess.

8. The suture anchor assembly of claim 1 further comprising a means to retain the expansion of the first body portion to secure the suture anchor assembly in the tissue.

9. The suture anchor assembly of claim 1 further comprising:
- the second body portion has a sharpened distal end to penetrate a bone;
- a delivery rod;
- a means to connect the delivery rod to the force connector whereby a retrograde force applied to the delivery rod is transferred to the second body portion;
- the force connector comprises a threaded recess in a connectable proximal end of the second body portion;
- the means to connect comprises a threaded distal end of the delivery rod configured to mate with the threaded recess;
- a means to retain the expansion of the first body portion to secure the suture anchor assembly in the bone;
- expansion fingers positioned between the distal and proximal collar whereby when the first body portion expands, the expansion fingers flexibly expand outward from the first body portion to secure the suture anchor assembly in the bone;
- the means to retain is at least one protrusion to engage the proximal collar; and
- the second body portion further comprises a suture tie whereby a suture can be retained by the suture tie to the second body portion.

10. An anchor assembly comprising:
- an expandable first body portion comprising at least one expansion finger;
- a second body portion having a sharpened distal end to penetrate bone; and
- the second body portion comprising a force connector whereby a retrograde force on the force connector forces the second body portion against the expandable first body portion and a forward force on the expandable first body portion forces the at least one expansion finger to expand to secure the anchor assembly in a tissue.

11. The anchor assembly of claim 10 further comprising:
- the expandable first body portion further comprising a proximal collar engaging the at least one expansion finger; and
- an impactor configured to transfer the forward force to the expandable first body portion.

12. The anchor assembly of claim 10 wherein the force connector comprises a threaded recess in a connectable proximal end of the second body portion and a means to connect comprises a threaded distal end of a delivery rod configured to mate with the threaded recess.

13. The anchor assembly of claim 10 wherein the first body portion comprises a resorbable material.

14. The anchor assembly of claim 10 wherein the second body portion further comprises a suture tie whereby the suture tie is configured to retain a suture to the second body portion.

15. The anchor assembly of claim 10 further comprising a means to retain the expansion of the first body portion to secure the anchor assembly in the tissue.

16. The anchor assembly of claim 15 wherein the means to retain is at least one protrusion to engage a proximal collar about the at least one expansion finger.

17. A method of anchoring a suture into a tissue, the method comprising:
- providing a suture anchor assembly comprising:
  - an expandable first body portion having a distal collar and a proximal collar,
  - a second body portion having a sharpened distal end to penetrate bone, and
  - the second body portion having a force connector whereby a retrograde force on the force connector forces the second body portion against the distal collar and a forward force on the proximal collar forces the first body portion to expand to secure the suture anchor assembly in a tissue;
- inserting the expandable first body portion and second body portion of the suture anchor assembly into a tissue;
- expanding the first body portion of the suture anchor assembly by applying a retrograde force to the force connector to secure the suture anchor assembly in the tissue; and
- attaching a suture to the suture anchor assembly.

18. The method of claim 17 wherein the tissue is bone.

19. The method of claim 17 wherein:
- the step of inserting the second body portion further includes applying a first forward force on the sharpened distal end of the second body portion; and
- the step of expanding the first body portion further includes applying the retrograde force to the distal collar of the first body portion and applying a second forward force on the proximal collar of the first body portion expanding the first body portion.

20. The method of claim 19 wherein the step of expanding the first body portion further includes:
- applying the retrograde force by forcing a wedge shaped proximal end of the second body portion into the distal collar of the first body portion and applying the second forward force with an impactor whereby the retrograde force and the second forward force expands an outer dimension of the first body portion.

* * * * *